United States Patent [19]

Ng et al.

[11] 4,391,801

[45] Jul. 5, 1983

[54] PLASMA PROTEIN FRACTION SUBSTANTIALLY FREE OF ACETATE IONS

[75] Inventors: Paul K. Ng, Hercules; Michael A. Fournel, Castro Valley, both of Calif.

[73] Assignee: Cutter Laboratories, Inc., Berkeley, Calif.

[21] Appl. No.: 316,201

[22] Filed: Oct. 29, 1981

[51] Int. Cl.$^3$ .................... A61K 37/02; A61K 37/04
[52] U.S. Cl. .................... 424/177; 424/101; 260/112 B
[58] Field of Search .............. 260/112 B; 424/101, 424/177

[56] References Cited

U.S. PATENT DOCUMENTS

| | | | |
|---|---|---|---|
| 2,390,074 | 2/1942 | Cohn | 260/122 |
| 2,958,628 | 11/1960 | Hink | 167/74 |
| 3,100,737 | 8/1963 | Auerswald | 167/74 |
| 3,876,775 | 4/1975 | Izaka | 424/177 |
| 4,017,470 | 4/1977 | Izaka | 260/112 B |
| 4,136,094 | 1/1979 | Condie | 260/122 |
| 4,251,510 | 2/1981 | Tankersley | 424/101 |

OTHER PUBLICATIONS

Chem. Abs. 88: 479e, 88: 83682q, 1978.
Olinger, G. N., Ann. Sur., vol. 190 (3), 305–311, 1979.

*Primary Examiner*—Allan Lieberman
*Assistant Examiner*—Patricia Short
*Attorney, Agent, or Firm*—Theodore J. Leitereg

[57] ABSTRACT

Stable plasma protein fractions (PPF) substantially free of vasodepressant amounts of acetate ions are disclosed. Solutions of the disclosed PPF are suitable for intravenous administration to patients without deleterious vasodepressor effects. Methods are also described for preparing the aforementioned PPF.

17 Claims, No Drawings

PLASMA PROTEIN FRACTION SUBSTANTIALLY FREE OF ACETATE IONS

BACKGROUND OF THE INVENTION

1. Field of the Invention

The invention relates to and has among its objects the provision of novel stable plasma protein fractions and methods for making them. It is a particular object of the invention to obtain Plasma Protein Fractions (Human) substantially free of acetate ions and such fractions substantially free of blood pressure depressant components. Further objects of the invention will be evident from the following description wherein parts and percentages are by weight unless specified otherwise.

2. Description of the Prior Art

Solutions of heat-treated human Plasma Protein Fractions (PPF), e.g., those described in U.S. Pat. No. 2,958,628, have enjoyed widespread medical utilization for conditions requiring the use of a plasma expander, such as shock, hypoproteinemia, and the like. The need for stable human PPF has been recognized since the discovery that pooled normal human plasma had a rather high rate of infection with the virus of homologous serum jaundice.

For the most part, solutions of PPF are administered to the patient at a slow rate with minimal side-effects. Recently, however, marked depression of blood pressure and alteration of coronary flow (hereinafter referred to as vasodepressor activity) have been observed in patients infused with PPF solutions at relatively rapid rates. For many patients this vasodepressor activity is extremely dangerous.

The presence of a "depressor substance" in human PPF was recognized in U.S. Pat. No. 2,958,628 (hereinafter '628). The depressant activity was ascribed to Fraction IV-1, and Hink et al in Vox Sang., Vol. 2, pages 174–186 (1957) note that removal of Fraction IV-1 from solutions of PPF results in a material with reduced depressor activity.

Further reduction of depressor activity was obtained in U.S. Pat. No. 3,876,775 (hereinafter '775). The patentees described the blood pressure depressant substance as a polypeptide having a molecular weight between 1,000 and 10,000 and being generated primarily during the heating of PPF solutions for sterilization purposes. In the process of '775 solutions of heat-treated PPF were contacted with a surface active adsorbent, a cation exchanger, an ultrafiltration membrane, or gel filtration particles.

In U.S. Pat. No. 4,251,510 there is disclosed a plasma protein fraction substantially free of bradykinin, kininogen, and prekallikrein activators, which were recognized as imparting vasodepressor activity to the protein fraction. In the patented process Hink Supernatant II plus III is treated at neutrality with a siliceous substance for a period of time sufficient to bring about essentially complete conversion of intrinsic kininogen to bradykinin. Subsequently, after being separated from Hink Fraction IV-1, the plasma protein fraction is reconstituted, held for a period of time sufficient to allow substantially complete destruction of bradykinin by carboxypeptidase, and subjected to ultrafiltration and/or diafiltration to remove ethanol and residual bradykinin. Then, the retentate is constituted with sodium caprylate, N-acetyl-dl-tryptophan, sodium carbonate, sodium chloride, and sodium acetate.

Recently, in the *Journal of Dialysis,* Vol. 2, No. 3, pages 235–242 (1978) and in the *Transactions of the American Society of Artificial Internal Organs,* Vol. XXIII, pages 399–405 (1977), it was disclosed that acetate ions caused blood pressure depression when used as a fixed base in hemodialysis treatment of renal failure.

Sodium acetate is employed in the current commercial productions of PPF (human). Sodium acetate, together with stabilizing agents, is added to the solution of dried powder obtained from drying a wet paste precipitated from Effluent IV-1 to increase the sodium ion concentration of the solution of human PPF to within the range required for medical use, namely, 130–160 milliequivalents per liter (meq/l).

SUMMARY OF THE INVENTION

We have discovered that the presence of acetate ions in solutions of PPF results in vasodepressor activity. In other words, acetate ions in the absence of known vasodepressants in human PPF yield a depression of blood pressure and increase in coronary arterial flow. One solution to this problem was to avoid addition of acetate ions in the manufacture of PPF; thus another sodium ion source, such as sodium chloride, was incorporated into a solution of PPF to raise its sodium ion concentration to within the above-mentioned range. We were surprised, however, that the resulting material still exhibited vasodepressor activity.

Our investigations have shown that solutions of human PPF precipitated from Supernatant IV-1 and processed under conditions wherein sodium acetate was not added to these solutions for the purpose of adjusting sodium ion concentration surprisingly contained about 2.5–5 meq/l of acetate ions ("endogenous" acetate). It may be that this endogenous acetate results from the acetate buffer system employed in the patented method of preparing human PPF, i.e., in the '628 process.

In addressing the above problem we have prepared a stable human PPF substantially free of vasodepressor activity and substantially free of acetate ions, i.e., containing less than about 2 meq of acetate ion per liter of PPF solution or free of vasodepressant amounts of acetate ion. In the process of the invention, diafiltration is applied to a solution of human PPF containing acetate ions to remove such ions. Then, the human PPF is stabilized, brought to certain required ionic concentrations in the absence of acetate ions, and pasteurized.

The primary advantage of the invention is that the improved human PPF may be administered to a patient at relatively rapid infusion rates without deleterious vasodepressor effects. As a consequence, solutions of PPF prepared by our process will enjoy broader application, and more people will be able to take advantage of the benefits of this useful plasma expander.

DESCRIPTION OF THE PREFERRED EMBODIMENTS

The starting material for the process of this invention is a plasma protein fraction which contains vasodepressant amounts of acetate ions. For example, a preferred starting material is plasma protein fraction (human) precipitated from Supernatant IV-1 obtained by the procedure of '628 (herein incorporated by reference). Plasma Protein Fraction (Human), PPF (Human) is the official nomenclature adapted by the U.S. Food and Drug Administration (FDA) 21 CFR 640.90 for the '628 product. PPF (Human) contains at least 83% albumin and no more than 17% alpha and beta globulin with no more than 1% gamma globulin. The process of the invention may also be applied to human plasma protein fractions produced by other methods such as the Rivanol ®-ammonium sulfate method and from other sources as known in the art, e.g., whole blood and placental blood. Customarily, human plasma protein fractions are pasteurized (heat-treated) in the presence of certain stabilizers to eliminate risk of hepatitis, i.e., to render them non-hepatitis infective.

In applying the process of our invention, Supernatant IV-1 of '628 is first treated to obtain a precipitated paste of plasma protein fraction by bringing the ethanol content of the supernatant to about 30 percent and lowering the pH to about 4.6, as known in the art. The paste is suspended in medically-acceptable water in which it subsequently dissolves. In accordance with the method of the invention, the solution is subjected to diafiltration following known procedures. To this end the suspension is passed through a membrane with a molecular weight cutoff value of 10,000, i.e., the membrane is permeable to substances with a molecular weight below about 10,000 and impermeable to those with molecular weights above about 10,000. Suitable membranes, by way of example and not limitation, that may be employed in this step of the present invention are Amicon PM10 and Amicon UM10 (Amicon Corp., Lexington, Mass.), Millipore PTGC (Millipore Corp., Bedford, Mass.), Romicon PM10 (Romicon Corp., Wicoburn, Mass.), and the like. Generally, the solution is passed through the membrane at a temperature greater than the freezing temperature of the mixture but not so great as to facilitate bacterial growth, that is, within the range of about 0°–35° C., preferably 2°–10° C. Diafiltration is continued until the acetate ion concentration is reduced to less than about 2 meq/l, preferably less than 1 meq/l, and more preferably to the level ordinarily found in human blood plasma, namely, 0.2–0.65 meq/l. Generally, 1 to 24 hours is sufficient to achieve this result. The time is dependent upon the size of the sample and the surface area of the membrane, the larger the sample and the smaller the surface area, the longer will be the period of diafiltration. During the period approximately 3–7 parts of diafiltrate are collected per part of original solution, i.e., the solution prior to application of diafiltration thereto. We have found the diafiltration step to be greater than 99% effective after 5 parts of diafiltrate are collected per part of original solution. The retentate contains human PPF substantially free of acetate ions.

The retentate is treated then to establish "final container" conditions as follows: To stabilize the PPF (Human) product sodium caprylate and N-acetyl-dl-tryptophan are added to the retentate according to the limits established by the FDA. In addition, sodium carbonate is added to adjust the pH to at least within the range established by the FDA, i.e., about 6.4–7.4, but preferably to a pH of about 6.7–7.3. Finally, enough sodium chloride is incorporated into the retentate to obtain a sodium ion concentration of about 130–160 meq/l as required by the FDA. It especially is to be noted that stabilization and pH and ionic concentration adjustment are accomplished in the absence of acetate ions.

The resultant retentate and product thus will possess the following concentration with respect to the recited materials: sodium ions, 130–160 meq/l; chloride ions 100–150 meq/l; caprylate ions, 3.2–4.8 meq/l; N-acetyl-dl-tryptophanate ions, 3.2–4.8 meq/l; potassium ions, less than 2 meq/l; protein, 4.7–5.3 percent; and acetate ions, less than about 2 meq/l. The retentate is clarified by filtration through non-asbestos filters, in the presence of no greater than about 0.5 grams of diatomite per liter. The clarified solution is held at about 2°–10° C. for at least about 48 hours and is heated for about 2–3 hours at 55°–65° C. and is cooled to below 10° C. without freezing. The heat treated solution is rendered sterile by filtration through an absolute filter, usually about 0.20 micron in size. The sterile bulk material is aseptically placed into sterile final containers and heated at about 60° C. for about 10 hours to pasteurize it.

It is further within the purview of this invention to dry the paste of PPF (Human) after precipitation from Effluent IV-1 obtained in the '628 procedure and then to prepare an aqueous solution, usually about 5% PPF (Human), of the dried powder. This aqueous PPF (Human) solution is subjected to diafiltration as described above to reduce the acetate ion concentration to less than about 2 meq/l, preferably less than 1 meq/l. Then, the solution is stabilized and adjusted to the proper pH and ionic concentration as mentioned above for the suspension of PPF (Human). Thereafter, the solution is heated as described above to pasteurize it.

In a less preferred embodiment of the present invention the aforementioned paste or powder can be formulated into an aqueous solution, which is brought to final container conditions by addition of the appropriate reagents, clarified, and sterile-filtered. The solution is heated at about 60° C. for about 10 hours to pasteurize it. Following pasteurization the solution is diafiltered under the above-described conditions to render it substantially free of acetate ions. Final container conditions again are secured and the material is placed in sterile final containers.

Another method for assuring the absence of acetate ions in our product is to employ a non-acetate buffering system throughout the '628 process. In other words, in the pH adjustment steps of '628 a pharmaceutically acceptable non-acetate buffering system is substituted for the sodium acetate-acetic acid system of the patented process. In this way a stable human PPF product having an acetate ion concentration less than about 2 meq/l is obtained.

It is, of course, important that known vasodepressor components such as bradykinin, prekallikrein activator and the like be removed where necessary to ensure that the product be substantially free of vasodepressor activity. This may be accomplished by known procedures such as those referred to above in the Description of the Prior Art. It is important to note that the diafiltration procedure will remove bradykinin from PPF containing such material.

EXAMPLES

The invention is further demonstrated by the following illustrative examples. The plasma protein fraction studied herein was PPF (Human) obtained by the process of Hink ('628); this product met the specifications for composition as expressed in sections 640.91 and 640.92 of Title 21 of the Code of Federal Regulations, herein incorporated by reference.

Animal Model

In the physiological experiments, dogs were anesthetized with intravenous injections of sodium pentobarbital, 30 mg/kg (Nembutal ®, Abbott Laboratories) intubated, placed in dorsal recumbancy, and ventilated on room air. A right femoral cutdown was made, and both vein and artery cannulated. The former was attached to a stop cock and test solutions were administered into it as well as supplemental anesthetic; the latter was attached to a Statham p23 db blood pressure transducer connected to a Grass Model 7 Polygraph and appropriate amplifiers for recording of systemic blood pressure.

The left chest was opened and a Statham Flowmeter Probe (non-invasive) was affixed to the left anterior descending coronary artery. The probe was connected to a Statham Model PS2002 Blood Flowmeter with the output displayed on the polygraph chart. Once the system reached stabilization, injections were administered intravenously at a rate 60 ml/minute, spaced by at least a five minute period. To provide accurate evaluation, all results were expressed as percent of control values.

Assay for Acetate

Acetate was measured by an enzymatic assay published by Bergmeyer ("Methods of Enzymatic Analysis", Vol. 1, p. 112, 1974). This is based on the conversion of acetate to acetyl-coenzyme A, which in turn reacts with oxaloacetate to form citric acid. The increase in absorbance at 340 nm, due to reduction of nicotinamide adenine dinucleotide in the enzymatic reaction, is proportional to the acetate concentration.

EXAMPLE 1

Endogenous Acetate in '628 Product

The product of '628 was prepared in a number of runs (A–F) and each was analyzed for acetate ion concentration by the aforementioned method.

The results are summarized below

| Sample | Acetate (meq/l) |
| --- | --- |
| A | 3.56 |
| B | 3.22 |
| C | 3.61 |
| D | 2.44 |
| E | 2.51 |
| F | 4.75 |

EXAMPLE 2

Comparison of Diafiltration and Ultrafiltration

The product of '628 was prepared, according to the patented procedure, as an acetone washed, air-dried powder. A 5% solution (2 l) Sample G, of this powder in water-for-injection (WFI) was prepared.

A portion (500 ml) of this solution (Sample I) was subjected to ultrafiltration according to the procedure outlined in Example 9 of '775. During the ultrafiltration the volume of solution was reduced to 100 ml.

Two 500 ml portions of the above solution were diafiltered using an Amicon PM10 membrane. Diafiltration was conducted against water for injection for a total of six [Sample H(2)] and five [Sample H(1)] volume exchanges, respectively.

The acetate ion concentration for each sample was determined by the aforementioned method.

The results are summarized below.

| Sample | | Acetate Level (meq/l) |
| --- | --- | --- |
| G | Starting material | 2.95 |
| H | Diafiltration | |
| | (1) Five volume exchanges | 0.59 |
| | (2) Six volume exchanges | 0.15 |
| I | Ultrafiltration | 1.97 |

EXAMPLE 3

The vasodepressor activities of Samples G and H(2) were determined using the above-described animal model. Also tested was Sample G with the addition of 10 meq/l (Sample J) and 20 meq/l (Sample K) of sodium acetate (NaAc). The results are tabularized below. Albumin (Human) (5%) was used as a comparison.

| Sample | Acetate Level (meq/l) | Mean Arterial Pressure (% change) | Coronary Artery Flow (% change) |
| --- | --- | --- | --- |
| H(2): Diafiltered | 0.15 | 2.0 | 10.3 |
| G: Starting Material | 2.95 | −0.3 | 13.3 |
| J: G + 10 meq/l NaAc | 12.95 | −3.0 | 67 |
| K: G + 20 meq/l NaAc | 22.95 | −11.0 | 112 |
| Control: | | | |
| 5% Albumin (Human) | 0 | 0.7 | 17.3 |

Having thus described the invention, what is claimed is:

1. A stable human plasma protein fraction precipitated from Supernatant IV-1 of the Cohn fractionation scheme as described in U.S. Pat. No. 2,958,628 wherein the plasma protein fraction consists essentially of at least eighty three percent albumin and no more than seventeen percent alpha and beta globulin and wherein the acetate ion concentration is about that ordinarily found in human blood plasma.

2. The fraction of claim 1 which further is substantially free of vasodepressor activity.

3. The fraction of claim 1 which further is substantially free of other vasodepressor components.

4. The fraction of claim 1 which further includes a stabilizer.

5. The fraction of claim 4 wherein the stabilizer is selected from the group consisting of sodium acetyltryptophanate, N-acetyltryptophan, and sodium caprylate.

6. The fraction of claim 1 which is further characterized as non-hepatitis infective.

7. A sterile aqueous solution of the stable plasma protein fraction of claim 1.

8. The solution of claim 7 which is suitable for rapid intravenous infusion without substantial vasodepressor activity.

9. The solution of claim 7 containing about five percent of stable plasma protein fraction.

10. The aqueous solution of claim 7 having a pH of about 6.4–7.4 and a composition which includes 130–160 milliequivalents per liter (meq/l) of sodium ions, 100–150 meq/l of chloride ions, stabilizing amounts of caprylate ions and N-acetyl-dl-tryptophanate ions, less than 2 meq/l of potassium ions, and containing about 4.7–5.3 percent protein.

11. The solution of claim 7 which is substantially free of vasodepressor activity.

12. The solution of claim 7 which is substantially free of other vasodepressor components.

13. A process for preparing the stable human plasma protein fraction of claim 1 which comprises the step of contacting an aqueous solution of stable human plasma protein fraction containing acetate ions with a diafiltration membrane having the capacity to allow acetate to pass therethrough but prevent passage of substantially all of the desired plasma proteins for a period sufficient to reduce the acetate ion concentration therein to a level ordinarily found in human blood plasma.

14. The process of claim 13 wherein the membrane has the capacity to allow substances with molecular weights below about 10,000 to pass therethrough but prevent the passage of substances with molecular weights above about 10,000.

15. The process of claim 13 which further comprises the step of heating the aqueous solution after contact with the membrane at a temperature of about 60° C. for a period of time to pasteurize it.

16. A process for preparing ths stable human plasma fraction of claim 1 which comprises the step of contacting an aqueous solution of stable human plasma protein fraction containing acetate ions with a diafiltration membrane having the capacity to allow acetate to pass therethrough but prevent passage of substantially all of the desired plasma proteins for a period sufficient to reduce acetate ion concentration therein to about 0.2–0.65 milliequivalents per liter.

17. A stable human plasma protein fraction precipitated from Supernatant IV-1 of the Cohn fractionation scheme as described in U.S. Pat. No. 2,958,628 wherein the plasma protein fraction consists essentially of at least eighty three percent albumin and no more than seventeen percent alpha and beta globulin and wherein the acetate ion concentration is about 0.2–0.65 milliequivalents per liter.

* * * * *